US009788999B2

(12) United States Patent
Schaller

(10) Patent No.: US 9,788,999 B2
(45) Date of Patent: Oct. 17, 2017

(54) FLOW PROMOTING OCULAR IMPLANT DEVICE AND METHODS

(71) Applicant: Novartis AG, Basel (CH)

(72) Inventor: Michael Schaller, Menlo Park, CA (US)

( * ) Notice: Subject to any disclaimer, the term of this patent is extended or adjusted under 35 U.S.C. 154(b) by 121 days.

(21) Appl. No.: 14/283,759

(22) Filed: May 21, 2014

(65) Prior Publication Data

US 2014/0364789 A1    Dec. 11, 2014

Related U.S. Application Data

(60) Provisional application No. 61/825,880, filed on May 21, 2013.

(51) Int. Cl.
*A61F 9/007*    (2006.01)

(52) U.S. Cl.
CPC ............................. *A61F 9/00781* (2013.01)

(58) Field of Classification Search
CPC .................................................. A61F 9/00781
See application file for complete search history.

(56) References Cited

U.S. PATENT DOCUMENTS

| 2004/0127843 | A1 | 7/2004 | Tu et al. |
| 2006/0024350 | A1* | 2/2006 | Varner ................. A61F 9/0017 424/427 |
| 2008/0125862 | A1 | 5/2008 | Blake |
| 2010/0316686 | A1* | 12/2010 | Dingeldein ........... A61L 27/306 424/422 |
| 2012/0035525 | A1 | 2/2012 | Silvestrini |
| 2012/0089071 | A1 | 4/2012 | Oliver et al. |

FOREIGN PATENT DOCUMENTS

| WO | WO-02/102274 A2 | 12/2002 |
| WO | WO 2014/043698 | 3/2014 |
| WO | WO 2014/078288 | 5/2014 |
| WO | WO 2014/190029 | 11/2014 |

* cited by examiner

*Primary Examiner* — Leslie Deak
(74) *Attorney, Agent, or Firm* — Fred C. Hernandez; Mintz Levin Cohn Ferris Glovsky and Popeo, P.C.

(57) ABSTRACT

Disclosed are devices and methods for treatment of eye disease such as glaucoma. Implants are described herein that create a flow field, such as between the anterior chamber and either the supraciliary space or suprachoroidal space. In addition, the implant can be treated with one or more treatments, including plasma treatments, for creating a variety of surface features and characteristics. Some of the surface features and characteristics can assist in controlling tissue responses to the implanted implant, including promoting or preventing tissue proliferation.

8 Claims, 15 Drawing Sheets

FLOW PROMOTING OCULAR IMPLANT DEVICE AND METHODS

CROSS-REFERENCE TO RELATED APPLICATIONS

This application claims priority to U.S. Provisional Application Ser. No. 61/825,880, titled, "Flow Promoting Ocular Implant Device and Methods," filed May 21, 2013, the disclosure of which is hereby incorporated by reference in its entirety herein.

BACKGROUND

The mechanisms that cause glaucoma are not completely known, though glaucoma has been linked to abnormally high pressure in the eye, which can lead to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Pursuant to such strategies, one or more implants can be delivered into the eye for shunting fluid out of the anterior chamber in order to regulate pressure in the eye. Accurate placement of an implant in the eye can be critical for the targeted effect of reducing intraocular pressure (IOP). For example, incorrectly placing an implant can inhibit aqueous outflow, such as if the incorrectly placed implant does not provide fluid communication with the flow target location.

Additionally, an ocular implant incorrectly placed in the eye, such as where a significant portion of the implant remains in the anterior chamber, damage to the corneal endothelium can result. For example, some incorrectly placed ocular implants, including implants that migrated after implantation, such as positioned too proximal in the angle of the ye, can touch the iris resulting in increased amounts of pigment dispersion in the eye which can increase outflow resistance and intraocular pressure by clogging the trabecular meshwork. Therefore, correct placement of the implant is desired for a safe and a successful surgical outcome.

Additionally, in at least some instances, reduction in IOP can be correlated with forming one or more areas of separation between parts of the eye, such as between the choroid and sclera. These areas of separation can at least assist in allowing fluid to flow from the anterior chamber of the eye to the suprachoroidal space or supraciliary space. However, although creating separation between parts of the eye may be beneficial, creating larger incisions in the eye is generally not. For instance, a larger diameter implant may be able to create greater separation between parts of the eye, such as between the sclera and choroid, but a larger incision would be necessary which can result in excess tissue damage to the eye.

Furthermore, after the implant has been implanted in a target location within the eye at least some of the tissue surrounding the implant can have a variety of responses to the presence of the implant. For example, some of the surrounding tissue can respond to the presence of the implant by proliferating tissue growth, such as connective tissue, around parts of the implant. Some tissue growth surrounding the implant can be beneficial for assisting in anchoring the implant and preventing implant migration. However, some tissue growth can impede fluid flow, including either through or surrounding the implant.

In view of the foregoing, there is a need for improved ocular implants which are compact enough such that they do not require a large incision for implantation but can provide improved separation between one or more parts of the eye, such as between the sclera and choroid, as well as assist in promoting fluid flow from the anterior chamber of the eye to the at least one of the suprachoroidal and supraciliary space. Additionally, there is a need for an implant to assist in controlling the tissue response of at least some of the tissue surrounding the implant in order to maintain an improved fluid flow created by the implant and reduce IOP.

SUMMARY

This disclosure relates generally to methods and devices for an ocular implant that can assist in reducing intraocular pressure (IOP), such as by promoting fluid flow from the anterior chamber of the eye to at least one of a suprachoroidal and supraciliary space. Some embodiments of the ocular implant disclosed herein include one or more or of a variety of surface features or characteristics along the length of the implant. For example, the surface features can assist the ocular implant in at least one of maintaining proper positioning within the eye and promoting fluid flow at least through the implant. In addition, the surface features or characteristics can create a variety of tissue responses at least surrounding a length of the implant, such as either promoting or preventing the proliferation of connective tissue.

In one aspect, there is disclosed an ocular implant for implanting in an eye that includes an elongate tubular body, a fenestration, an extruded feature, and a surface feature. The elongate tubular body of the ocular implant includes a proximal end, a distal end and an inner lumen extending at least partway between the proximal end and the distal end. In the ocular implant, the fenestration extends from an outer surface of the tubular body and intersects with the inner lumen of the tubular body. The extruded feature of the ocular implant extends from the outer surface of the tubular body adjacent the proximal end. The surface feature of the ocular implant is configured to alter an ocular tissue response to the implant.

In a related aspect, there is disclosed a method of treating an ocular implant for creating surface features that includes treating the ocular implant with a plasma treatment that is configured to alter a tissue response of the implant. The ocular implant treated in the method includes an elongate tubular body that includes a proximal end, a distal end and an inner lumen extending at least partway between the proximal end and the distal end. The implant treated in the method has a fenestration extending from an outer surface of the tubular body and intersecting with the inner lumen, and the implant includes an extruded feature extending from the outer surface of the tubular body adjacent the proximal end.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings.

Like reference symbols in the various drawings indicate like elements.

DETAILED DESCRIPTION

This disclosure relates generally to methods and devices for an ocular implant that can assist in reducing intraocular pressure (IOP), such as by promoting fluid flow from the anterior chamber of the eye to at least one of a suprachoroidal and supraciliary space. Some embodiments of the ocular implant disclosed herein include one or more or of a variety of surface features or characteristics along the length of the implant. For example, the surface features can assist the ocular implant in at least one of maintaining proper positioning within the eye and promoting fluid flow at least through the implant. In addition, the surface features or characteristics can create a variety of tissue responses at least surrounding a length of the implant, such as either promoting or preventing the proliferation of connective tissue.

Figure 1:
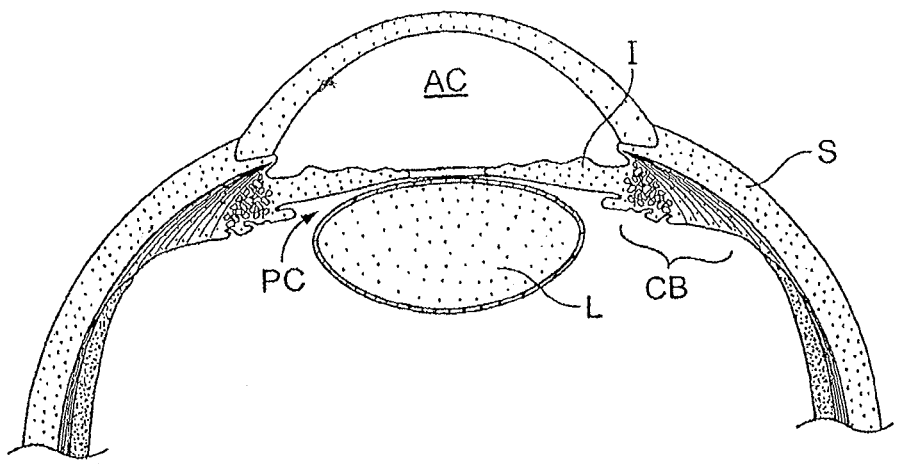
FIG. 1 shows an example cross-sectional view of a portion of the human eye.

FIG. 1 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris through which light passes. The volume between the iris and the lens is the posterior chamber PC. The volume between the iris and the cornea is the anterior chamber AC. Both chambers are filled with a clear liquid known as aqueous humor.

Figure 2:
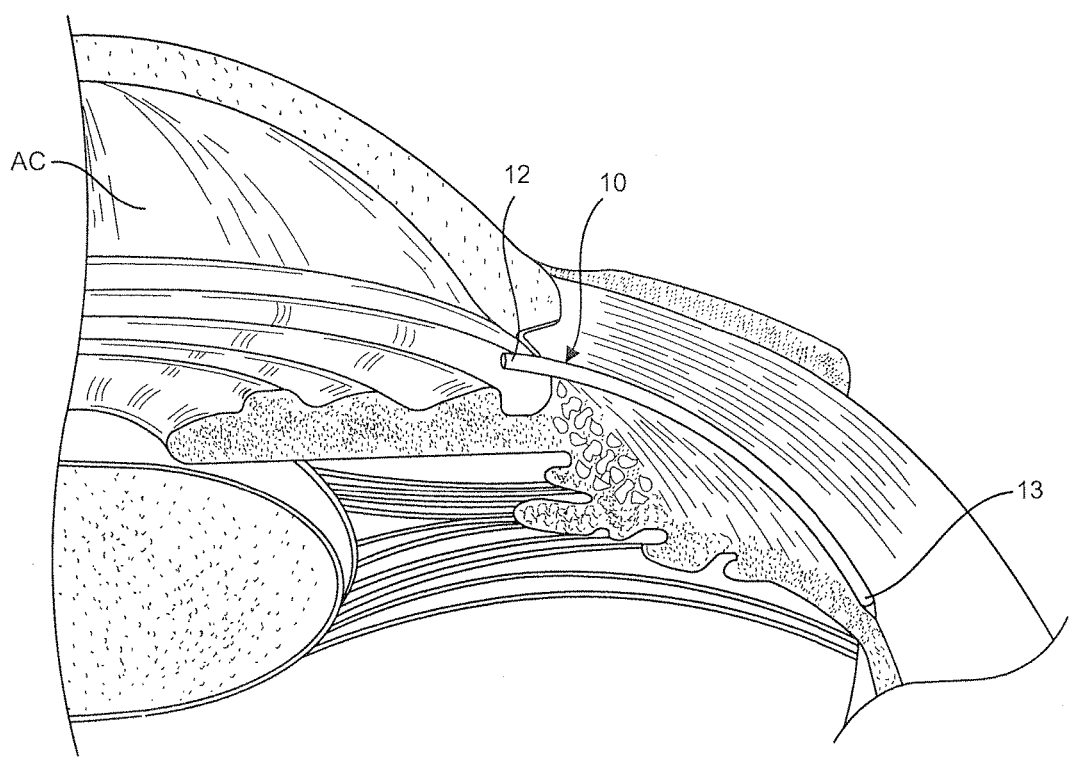
FIG. 2 shows and an example cross-sectional perspective view of a portion of the eye showing a part of the anterior and posterior chambers of the eye and a schematic representation of an embodiment of an implant positioned inside the eye such that a proximal end is located in the anterior chamber and a distal end communicates with and/or is located in or near the supraciliary space.

FIG. 2 is a cross-sectional, perspective view of a portion of the eye showing the anterior and posterior chambers of the eye. A schematic representation of an embodiment of an implant 10 is shown positioned inside the eye such that a proximal end 12 is located in the anterior chamber and a distal end 13 communicates with and/or is located in or near the supraciliary space. In another embodiment, the distal end 13 is located in the suprachoroidal space. It should be appreciated that FIG. 1 and other figures herein are schematic and are not necessarily to scale with respect to size and relative positions of actual eye tissue.

The ocular implants disclosed herein can provide a fluid pathway between at least the anterior chamber and either the supraciliary space or suprachoroidal space. For example, the implant can include a distal end that can be positioned in the supraciliary space or the suprachoroidal space. The implant may be positioned at least partially between the ciliary body and the sclera or it may be at least partially positioned between the sclera and the choroid. The distal end of the implant may be positioned between other anatomical parts of the eye.

In some embodiments, the implant can include an elongated tubular body having one or more internal lumens through which aqueous humor can flow, such as from the anterior chamber into either the suprachoroidal or supraciliary space. The implant can have a substantially uniform internal diameter along its entire length, although the shape of the implant can vary, such as along its length. Alternatively, the implant can have a variable internal diameter along its length. Moreover, the implant can have various cross-sectional shapes, such as a circular, oval or rectangular shape, and can vary in cross-sectional shape moving along its length. For example, the cross-sectional shape can be selected to facilitate easy insertion into the eye.

The internal lumen of the implant can serve as a passageway for the flow of aqueous humor through the implant directly from the anterior chamber toward or into the suprachoroidal space or supraciliary space. In addition, the internal lumen of the implant can be used as an access location to mount the implant onto a delivery system. The internal lumen can also be used as a pathway for flowing fluid, such as an irrigation fluid or a visco-elastic substance, into the eye for flushing or to maintain pressure in the anterior chamber, or using the fluid to assist in dissection, visualization or hydraulic creation of a dissection plane into or within the supraciliary or suprachoroidal space. Fluid can be flowed toward or into either the supraciliary or suprachoroidal space, for example via a delivery cannula or through the internal lumen of the shunt. The fluid can be flowed into the eye with a pressure sufficient to form a dissection plane in or within the supraciliary or suprachoroidal space. The fluid can accumulate within the eye so as to form a lake. In general, hydro-dissection or the injection of fluids such as visco-elastic substances can be used to separate the ciliary body from the sclera to enlarge an area of detachment of the ciliary body from the sclera with or without insertion of a device.

Figure 3:
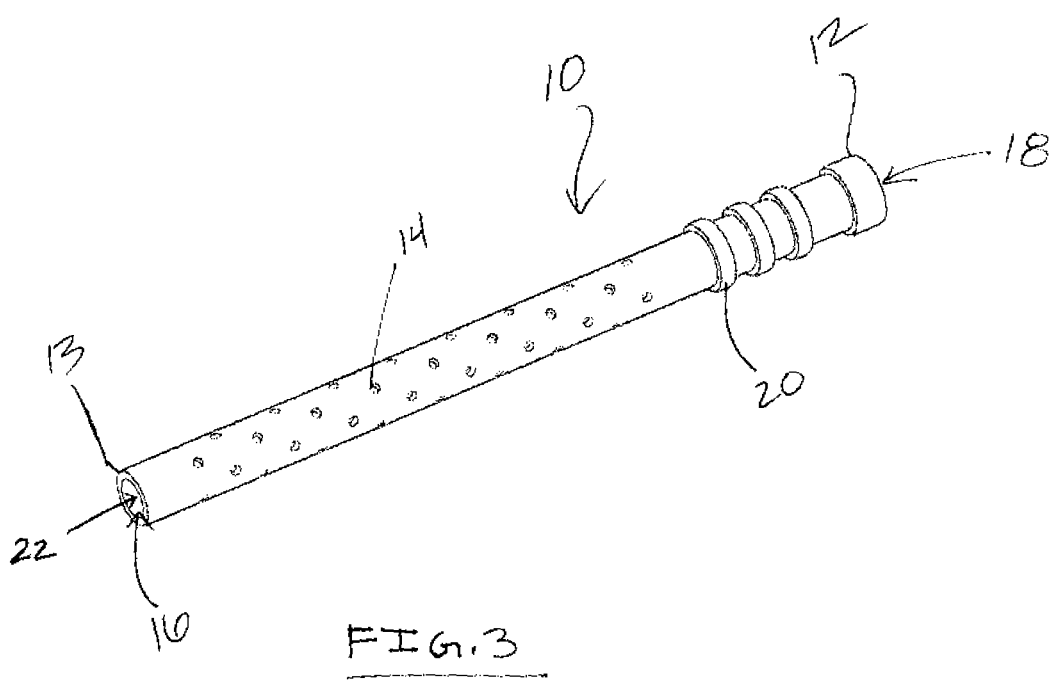
FIG. 3 shows an isometric view of an embodiment of the ocular implant.

FIG. 3 illustrates an embodiment of an ocular implant 10 having a tubular structure with an inner lumen 22 which can extend through the length of the implant 10. In addition, the implant 10 can include at least one fenestration 14 along the length of the implant 10. The fenestrations 14 can provide a fluid passageway between one or more areas surrounding the implant 10 and the inner lumen 22 of the implant 10. Additionally, the fenestrations 14 can assist in promoting flow through the implant 10, such as aqueous fluid, in order to reduce IOP.

For example, the fenestrations 14 can provide additional fluid passageways through the implant 10 other than though a main outlet port 16 at the distal end of the implant 20 or a main inlet port 18 at the proximal end of the implant 10. In addition, in the event either the main outlet port 16 or the main inlet port 18 of the implant 10 is occluded, the fenestrations 14 can provide alternate fluid passageways for fluid flowing through the implant 10, such as aqueous fluid flowing from the anterior chamber into the suprachoroidal space or supraciliary space.

Any number of fenestrations 14, which can vary in shape and size, can be positioned anywhere along the length of the implant 10. Additionally, the density of fenestrations 14 along the length of the implant 10 can vary. For example, more fenestrations 14 may be positioned near the distal end of the implant 10 than near the proximal end. As shown in FIG. 3, more fenestrations can be positioned adjacent the distal end than adjacent the proximal end which can assist in promoting a distally directed fluid flow, such as by the formation of a pressure gradient. This can be beneficial when the proximal end of the implant is positioned at least partly in, for example, the anterior chamber and the distal end is positioned in the suprachoroidal or supraciliary space for treatment of an eye having high IOP.

In addition, FIG. 3 illustrates an ocular implant 10 having one or more retention rings 20 extending from the outer surface of the implant 10. The retention rings 20 can be positioned at or near the proximal end of the implant 10 for assisting in preventing occlusion and providing additional retention and assist in preventing against migration of the implant 10 after implantation. The size and shape of the retention rings 20 may vary and any number of retention rings 20 can extend along the length of an implant 10.

Figure 4:
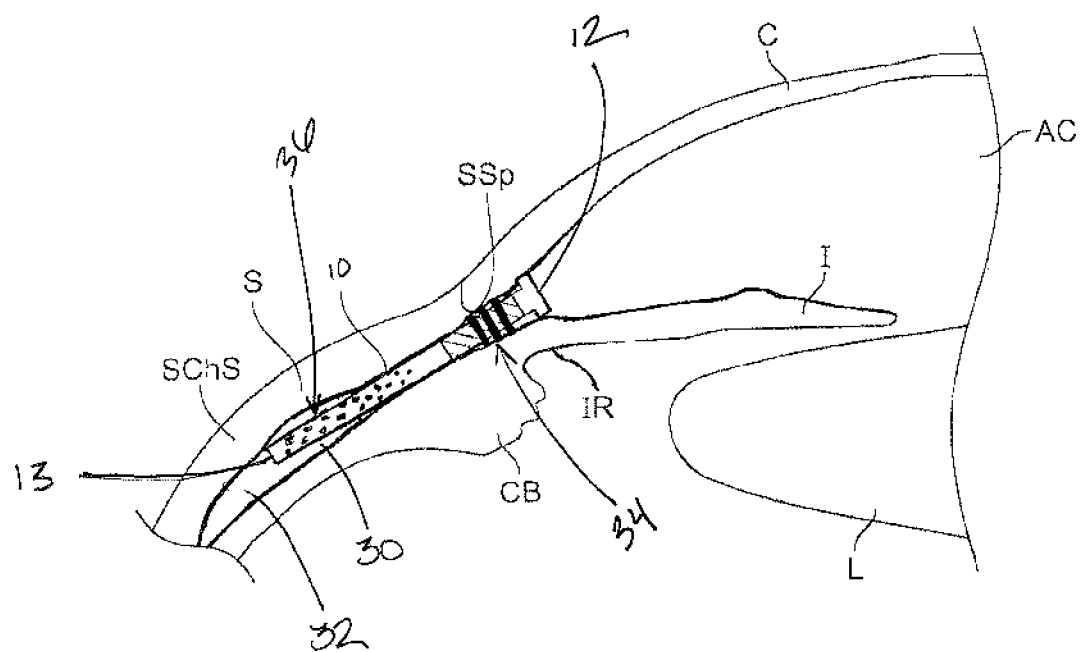
FIG. 4 shows an enlarged view of a section of an eye with an implant implanted in an implantation site and the formation of tissue separation surrounding parts of the implant for promoting fluid flow.

As shown in FIG. 4, in an implanted state, the implant 10 can create an area of separation 30 between the choroid and sclera around at least a part of the implant (also known as "tenting") and a space 32 created around, for example, the most distal portion of the implant (also known as an "aqueous lake"). In addition, increasing the area of scleral and choroidal separation can improve IOP reduction in at least some instances.

Although increasing the area of scleral and choroidal separation can be advantageous, several drawbacks can occur if a lager implant, such as an implant larger than approximately 0.5-1.0 mm in diameter, is used to create the larger separation. For example, some drawbacks may include the requirement for a larger incision, such as along the limbus, due to a greater diameter implant. A larger incision may cause fluids to escape the eye, such as at least from the anterior chamber, and complicate the implantation procedure. For example, an incision less than 2.5 mm may be preferable for implantation of at least one implant.

Other drawbacks to using a larger diameter implant can include creating a larger cyclodialysis which may result in increased rates of hypotony post operatively and increased rates of retinal detachments. In addition, a larger implant can be more difficult to insert into the supraciliary and suprachoroidal space due to the requirement of greater tissue separation which may result in excess tissue damage. Therefore, an implant which is sized such that it does not require a large incision (such as less than 2.5 mm) and can promote the flow of aqueous fluid from the anterior chamber of the eye to the suprachoroidal space or supraciliary space may overcome the drawbacks discussed above while achieving an improved reduction in IOP.

The present disclosure includes various embodiments of ocular implants 10. For example, the proximal end 12 can be configured to be positioned in the eye such that it allows aqueous fluid to flow into the inner lumen 22 of the implant 10. The distal end 13 of the implant 10 can be configured and positioned in the eye such that it allows aqueous fluid to flow out of the implant 10. In addition, the proximal end 12 and distal end 13 of the implant 10 can include features that assist in promoting fluid flow through the implant 10 and protect the eye from damage. Additionally, the implant 10 can include one or more of a variety of surface features or characteristics which can assist the implant 10 in at least either maintaining the implanted position of the implant 10 or promoting fluid flow.

As discussed above, increasing the area of scleral and choroidal separation 30 and the formation of an aqueous lake 32 can improve IOP reduction in at least some instances. However, over time, connective tissue can proliferate around parts of the implant 10 and can ultimately secure to parts of the implant 10. The proliferation of connective tissue can be advantageous in some respects in order to prevent migration of the implant 10 after implantation. In particular, it can be advantageous for connective tissue to secure a length along the proximal end 12 of the implant in order to prevent implant migration. Although it may be advantageous for connective tissue to secure one or more parts of the implant 10, it can be disadvantageous for connective tissue to secure or proliferate around other parts of the implant 10.

For example, after implantation, some parts of the implant 10 are not initially in contact with surrounding tissue because the implant 10 has created either tenting 30 or aqueous lake 32 effects. In addition, the space created around the implant 10 from tenting 30 and aqueous lake 32 can assist in reducing IOP. Therefore, the parts of the implant 10 which do not contact tissue in order to assist in creating either tenting 30 or aqueous lake 32 effects can benefit by preventing connective tissue from securing or proliferating around these parts of the implant.

In some embodiments, the implant 10 can include one or more surface features or characteristics which create a variety of tissue responses to the implant. For example, some surface features or characteristics can promote or prevent the proliferation of connective tissue. As shown in FIG. 4, some implants can have a first length 34 adjacent the proximal end 12 of the implant 10 having a first type of surface treatment or characteristic and a second length 36 adjacent the distal end 13 of the implant 10 having a second type of surface treatment or characteristic. In some embodiments, the first type of surface treatment or characteristic can promote tissue proliferation and the second type of surface treatment or characteristic can prevent or minimize tissue proliferation. This can allow the proximal end 12 to assist in preventing implant migration and allow the distal end 13 to assist in preventing or minimizing tissue growth and disturbing tenting 30 and aqueous lake 32 effects.

One or more of a variety of surface treatments can be performed on an implant 10 in order to achieve a variety of surface topographies or surface chemistries which can create one or more desired effects, such as a variety of responses from tissue surrounding the implant, including promoting or preventing tissue proliferation. For example, one or more plasma treatments can be used to modify the surface of the implant 10. At least some plasma treatments use gases which are excited to a higher state of energy, also known as plasma, in order to modify the one or more materials comprising at least the surface of the implant 10. The materials and settings of the plasma treatments can create a variety of surface topographies and characteristics, as will be discussed, for example, in greater detail below.

In some embodiments, the plasma treatment can use one or more inert gas such as $H_2$, $O_2$, $N_2$, or the like. Alternatively or in addition, the plasma treatment can use molecules such as $C_4F$ or any other appropriate gas. In some embodiments, the plasma can attack the surface of the implant 10 and break away molecules, or the like, from the surface. For example, plasma treatments can be used to clean the implant 10 by removing surface level contaminants or impurities.

There are a variety of plasma treatment methods which may be used such as activation, plasma-enhanced chemical vapor deposition (PECVD), grafting, and hybrid processes. Activation may employ gases or vaporized liquids which are either incapable of polymerizing or are conducted with process parameters non-conducive to polymerization. PECVD may employ gases, typically carbon containing, that are either reactive and prone to polymerization such as ethylene or vinyl benzene (styrene) or under the influence of appropriate plasma conditions fragment to form reactive species that recombine to form higher molecular weight materials that deposit on a substrate to form a coating. Grafting while similar to PECVD is differentiated by the intention of providing functional groups without creating a discrete material layer. Reactive monomers capable of polymerizing are used but the plasma parameters are judiciously chosen to avoid creating a separate layer on the surface. One example would be using trimethoxyaminopropylsilane [(CH3O)3SiCH2CH2CH2NH2] to attach a gamma pendant primary amine group along the substrates backbone (bb) [bb-O—SiCH2CH2CH2NH2]. A hybrid process uses a combination of processes including wet or gas phase chemistry, UV irradiation, etc. to accomplish the desired surfaces.

Different Types of Plasma Treatments

Any of the plasma treatments described herein may be used. Certain plasma treatments may alter the top surface micro-layer of the substrate material without the adding materials as described in certain embodiments of the activation plasma treatments. These plasma treatments may additionally etch or ablate the top surface of the substrate material to create the surface topographies as described herein. Alternatively, other plasma treatment methods may be utilized which deposit a micro-layer of material that is different from the substrate material. Any number of plasma treatment processes may be used to alter the surface chemistry or surface topography of the implant. Several embodiments of such treatments are described herein.

In some embodiments, plasma treatments can be used to alter the surface topography of the implant 10, such as to create one or more surface features or surface characteristics described herein, including a variety of peaks and valleys. Alternatively or in addition, plasma treatments can deposit material onto the surface of the implant 10 in order to create a desired surface topography along at least a part of the implant 10. Additionally, any one or more plasma treatments can be applied to the implant 10 in whole or part. Therefore, more than one area of surface features or characteristics can be positioned along the surface of the implant 10. As discussed above, the variety of surface features and characteristics can create a variety of tissue responses, including either promoting or preventing the proliferation of connective tissue.

In some embodiments of the plasma treatment process, hexafluoropropylene (HFP), an oxygen rich hydrocarbon, can be used in order to deposit a similar or different material onto the surface of the implant 10. The HFP, or other material, can assist in at least one of altering the surface topography of the implant 10 or providing one or more characteristics, such as create hydrophobic or hydrophilic coatings. For example, the hydrophobic or hydrophilic coatings can alter the interaction of the surface of the implant 10 with surrounding tissue, including promoting or preventing direct contact between the surfaces of the implant 10 and surrounding tissue.

Alternatively, the plasma treatment may be utilized to create altered surface chemistries along the top surface of the implant. These altered layers of surface chemistry may be between 1 and 1000 angstroms thick such as 200 angstroms (0.02 micrometers). Alternatively, the altered surface chemistries may be thicker or thinner. The micro-layers of material may be created by altering the top layer of the substrate material. Alternatively, the micro-layer may be created by adding a layer of material on top of the substrate material as may be the result of PECVD plasma treatments. The surface chemistries created may be chosen specifically to alter the tissue response to the implant. For example, while in-vitro and in-vivo experiments exist which evaluate the biocompatibility and tissue response of various materials, these studies may at times be conflicting in what is considered the optimal surface chemistry. However, certain materials exist which are generally considered good candidates for implant materials due to their historical usage in implantable medical devices. For example, polyolefin resins such as polyethylene or polypropylene are generally considered biocompatible and exhibit an acceptable tissue response. Additionally, fluoropolymers such as PTFE also exhibit suitable properties. Additionally, polyethylene glycol derivatives such as polyethylene oxide resin also known as PEG resins also exhibit suitable properties. Alternatively, any number of other materials exist which exhibit suitable biocompatible and tissue response characteristics.

A variety of plasma treatment processes may be used to create micro-layers of these materials on the surface of the implant. For example, the PEVCD process may be used. In one embodiment, to create a polyethylene surface, the implant may first be plasma treated with O2 and CF4 in an activation plasma treatment to prepare the surface. Then a second plasma treatment utilizing the PECVD method may be used with a C2H4 gas. This may be followed by a quenching treatment of C2H4 and Argon. The process parameters such as power, pressure, time and temperature within the plasma chamber may be altered accordingly to create the desired surface material. Additionally, any number of plasma treatment processes may exist to create the desired surface material. This may include a single plasma treatment or multiple plasma treatments and any number of quenching steps. In an alternate embodiment, to create a surface material with characteristics to the fluoropolymer FEP the following processes may be utilized. The implant may be first plasma treated with O2 and CF4 in an activation plasma treatment to prepare the surface. Then a second plasma treatment utilizing a PECVD method may be used with a HFP gas and pulsed power. This may be followed by a quenching treatment of HFP and Argon.

In other embodiments, the surface chemistry of the implant may be altered through other techniques. For example, it is understood that certain materials such as polyimide may change chemically when exposed to radiation. Certain sterilization methods for medical implant such as e-beam sterilization and gamma irradiation expose the implant to radiation. In these examples, the gas surrounding the implant during the sterilization process may affect the surface chemistry. For example, oxygen present in the sealed packaging of the implant may alter the surface chemistry of the implant during the radiation exposure during sterilization.

Still other methods of altering the surface chemistry of the implant may exist including dip coating and spray coating.

Various processes and treatments, such as plasma treatments, can be used at different locations along the implant 10. For example, some plasma treatment can be used which creates a surface topography that minimizes cellular reaction and cellular adherence to the surface of the implant 10. In addition, such plasma treatments can be applied to a distal area of the implant 10 in order to allow the implant to create and maintain either tenting or aqueous lake effects without connective tissue growth impeding fluid flow.

In some embodiments where surface topology or characteristics from one or more plasma treatments are desired along only a part of the implant 10, a mask can be used to cover the parts of the implant 10 which are not intended to be exposed to the plasma treatment. In this way, one or more parts of the implant 10 can be treated with a plasma treatment without affecting the other parts of the implant.

For example, the proximal end 12 of the implant 10 can be masked in order to expose the distal end 13 of the implant to a first plasma treatment, such as one which creates surface topology that prevents connective tissue adherence or proliferation. In addition, after treatment of the distal end 13, the proximal end 12 can be uncovered by the mask and the distal end 13 can be covered by the mask in order to expose the proximal end 12 of the implant 10 to a second plasma treatment, such as one which creates surface topology or characteristics which promote cellular growth and tissue adherence to the implant which can assist in preventing implant migration. Any number of plasma treatments applied to any number of parts and areas of the implant 10 can be done in order to create a variety of surface features and characteristics along the implant 10.

In addition, the surface topography of the implant can include one or more of a variety of surface characteristics along at least a part of the surface of the implant in order to assist in creating one or more desired effects. In addition, the surface characteristics can be formed by any of the treatments, such as the plasma treatments, laser ablation techniques, or the like, discussed herein. For example, the surface topography can include one or more peaks and valleys along the surface of the implant 10. The peaks and valleys can form a variety of patterns, including an even pattern having equal spacing and feature dimensions. For example, in some embodiments, the peaks and valleys can have lengths approximately 0.1 microns to 20 microns. In some embodiments, the peaks and valleys are at least one of unevenly spaced and are unequally dimensioned. In addition, some surface topography can include a series of valleys and peaks which create a stepped appearance, such as more than two peaks extruding from the surface at increasing distances.

In some embodiments, the pattern of peaks and valleys can be irregular, such as a long peak that is approximately 6 microns can be followed by a short valley that is approximately 1 micron which can be followed by a short peak that is approximately 2 microns which can be followed by a long valley that is approximately 5 microns. Any number of peaks and valleys having any number of sizes and dimensions can be included in the surface topography of the implant 10 in order to create a variety of tissue responses from at least tissue surrounding a part of the implant.

The transition between a peak and a valley may be a sharp transition, such as a transition which is approximately perpendicular to the surface of the implant prior to processing and creation of the peaks and valleys. Alternatively or in addition, the transition between a peak and a valley can be angled, such as similar to a chamfer, or a rolling transition, such as similar to a sinusoidal wave. In addition, the peaks and valleys can run radially along at least a part of the implant 10, such as similar to a series of rings. Alternatively or in addition, the peaks and valleys can run longitudinally along at least a part of the implant, such as similar to a series of stripes. Furthermore, multiple patters of peaks and valleys can run in a variety of directions which can create a cross hatch pattern, or the like. Any number of patterns of raised and lowered surfaces, such as peaks and valleys, can be included along the surface of the implant.

Furthermore, any one or more surface treatments and surface characteristics can be included along any one or more parts or lengths of the implant 10 in order to achieve one or more desired effects, such as preventing or promoting the proliferation of connective tissue along the parts and lengths of the implant 10. In addition, one or more coatings, such as drugs or materials which create a variety of tissue responses, can coat any one or more parts of the implant 10.

In some embodiments, the surface treatments or surface characteristics can create a variety of surface topographies. For example, the surface topographies can reduce the amount of contact area between the surface of the implant and a surrounding tissue cell. For example, the implant 10 can undergo at least one of the surface treatments which can create a series of peaks and valleys that occur at a linear frequency of about 1%-100% of the length of a typical cell. In some embodiments, the length of a peak may be approximately 2 microns to approximately 5 microns, or approximately 3 microns, and the length of a valley may be approximately 2 microns to approximately 5 microns, or approximately 3 microns. Therefore, a tissue cell which may be approximately 10 microns long and resting against the surface of the implant may contact approximately 1-2 implant surface peaks. The observed contact area that the tissue cell makes with the implant 10 surface may therefore be approximately 30-60% of the overall length of the tissue cell. Since a smaller contact area is created between the tissue cell and the surface of the implant (i.e., less that 100% contact between the surface of the implant and the tissue cell), the cell may have a lower reaction to the surface than a surface that is completely flat (i.e., resulting in approximately 100% contact between the surface of the implant and the tissue cell). Furthermore, in at least some cases, a cell which has a lower reaction to the surface of the implant can either limit or prevent the proliferation of connective tissue and adherence of the tissue to the implant 10. This can at least minimize tissue growth surrounding the implant 10 that can impede fluid flow through and around the implant 10.

The surface features described herein may be created using any number of manufacturing methods or processes. Plasma treatment may be a suitable method for altering the surface topography of the implant. Alternatively, laser ablation may be utilized to create any number of surface topographies.

In some embodiments the surface topographies described herein may include grooves along the length of the implant. For example, a series of micro-grooves may be created on the surface of the implant to create a set of peaks and valleys. The micro-grooves may be cut such that they align along the length of the implant. Alternatively, the micro-groove may exist in a radial pattern along the length of the implant. Alternatively, the micro-grooves may create a spiral pattern down the length of the implant. Any other number of suitable orientations of the micro-grooves may exist. The micro-grooves may be on the order of 0.0001" to 0.0040" in width from peak to peak and from 0.0001" to 0.0040" in height differential between the peaks and valleys. The slopes of the peaks and valleys may be vertical or sloped any appropriate amount. The corners may be sharp or may include any number of sized radii or chamfers.

Some implementations of the implant can include at least one fenestration. Any one fenestration can be placed anywhere along the implant, including at the proximal end, distal end, or along the length of the implant, for assisting in fluid flow through the implant. In addition, the fenestrations can have any number of a variety of sizes and shapes and can be arranged in any number of a variety of patterns along the implant.

Some implementations of the implant can include one or more extruded features or indented features which can assist with at least one of fluid flow, alter tissue response to the implant, or anchor the implant and prevent implant migration within the eye. For example, one or more extruded features, such as pegs or rings, can be positioned adjacent or near one or more fenestrations, including the main inlet and outlet port of the implant. Furthermore, one or more indented features can be positioned along a length of the implant for assisting in altering the tissue response to the implant, such as prevent the adjacent ocular tissue from adhering to the implant along the length of the implant.

Figure 5:
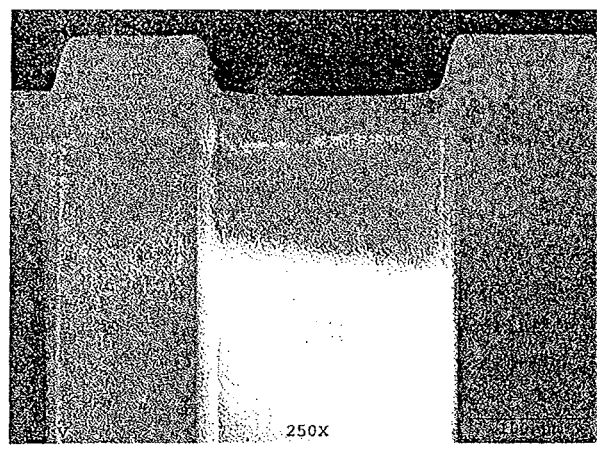
FIG. 5 shows a scanning electron microscope (SEM) image of a part of the implant, including a pair of retention rings, before any surface processing.
Figure 6:
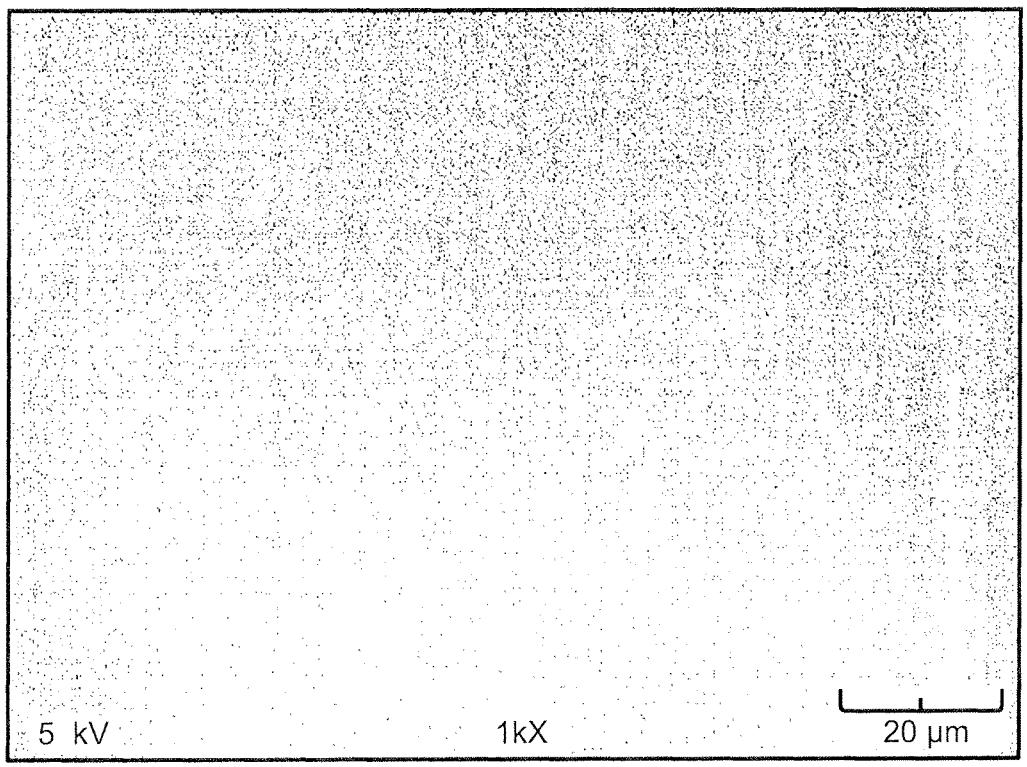
FIG. 6 shows a magnified SEM image of the retention rings shown in FIG. 5 before any surface processing.
Figure 7:
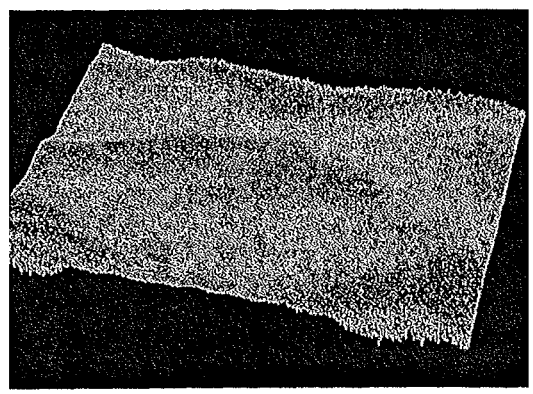
FIG. 7 shows an optical profilometry (OP) scan image of the surface of the implant of FIG. 5 before any surface processing.

FIGS. 5 and 6 illustrate an example of a scanning electron microscopy (SEM) image showing a surface of an embodiment of an implant 10, including a pair of retention rings 20. In this example, no surface treatments were performed on the implant 10 shown in FIGS. 5 and 6 prior to taking the SEM image. For example, the implant 10 can be made out of polyimide tubing and manufactured through a dip-coating process and then laser ablated to create the retention rings 20. FIG. 7 shows an example image from an OP (optical profilometry) scan of the same implant 10 embodiments shown in FIGS. 5 and 6. These figures can provide an example of the surface of the implant 10 without any surface treatment.

Figure 8:
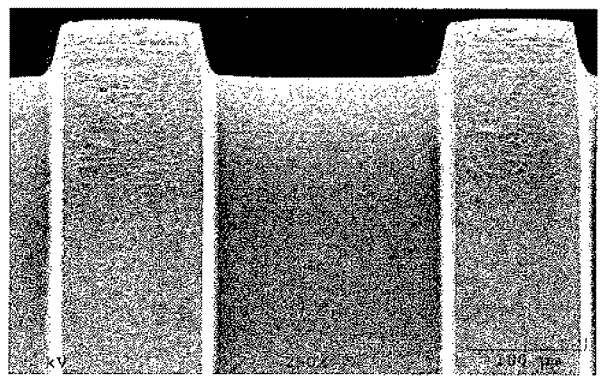
FIG. 8 shows an SEM image of the implant and retention rings shown in FIG. 5 after plasma treatment with $CF_4+O_2$.
Figure 9:
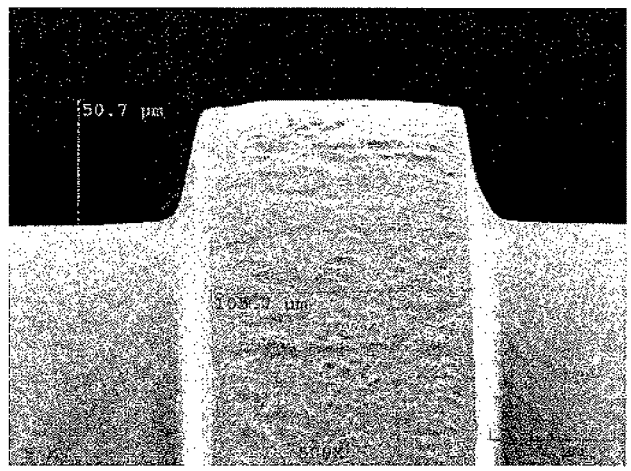
FIG. 9 shows an SEM image of the implant shown in FIG. 8 after plasma treatment with $CF_4+O_2$ under a higher magnification.
Figure 10:
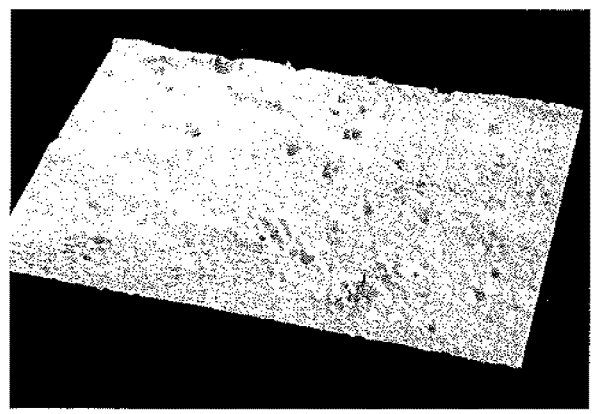
FIG. 10 shows an OP scan image of the implant shown in FIG. 8 after plasma treatment with $CF_4+O_2$.

FIG. 8 and FIG. 9 illustrate example SEM images of the implant 10 after having undergone a plasma treatment of $CF_4+O_2$ at approximately 200 W for approximately 12 minutes. Some embodiments of the implant 10 can undergo a plasma treatment of $CF_4+O_2$ at approximately 150 W to approximately 250 W for approximately 10 minutes to approximately 15 minutes. In some implementations, any of the above plasma treatments of $CF_4+O_2$ at a variety of Watts for a variety of minutes can be used to clean the surface of the implant 10. The images provided in FIGS. 8 and 9 can show a difference in surface topography that may appear cleaner than the implant 10 that has not undergone a plasma treatment. In addition, FIG. 10 shows an example image from an OP scan which shows the surface of the same implant 10 as shown in FIGS. 8 and 9. In general, the surface may appear flatter but with more abrupt features such as pock marks, divots, peaks, valleys, and the like.

Figure 11:
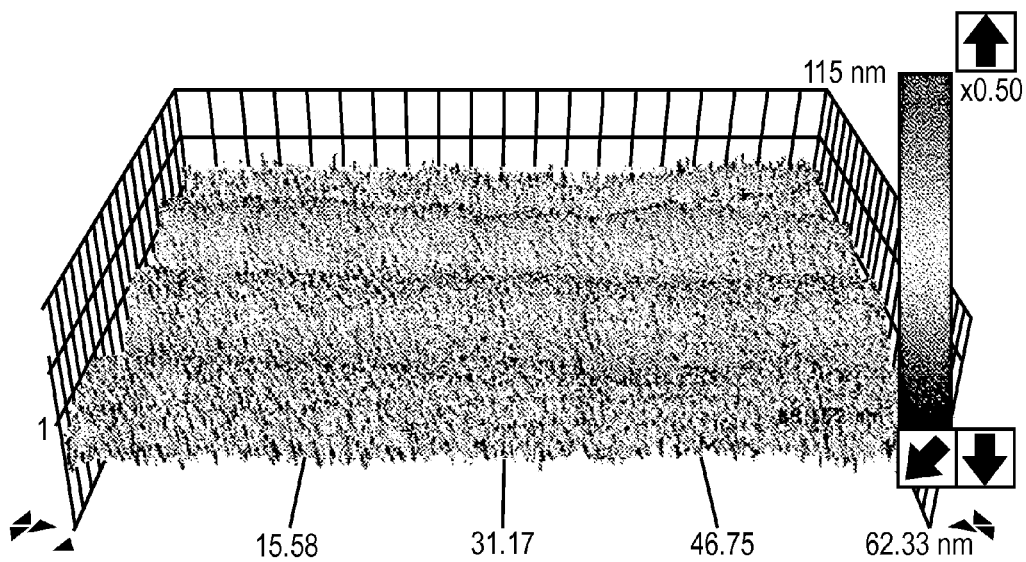
FIG. 11 shows an OP scan image of an implant surface after plasma treatment with $O_2$.

FIG. 11 illustrates an example image from an OP scan of an embodiment of the implant 10 which has undergone a plasma treatment with $O_2$. For example, the plasma treatment with $O_2$ can create undulating peaks and valleys on the surface of the implant 10 which can occur at either regular or irregular intervals or patterns along the length of the implant 10. In some embodiments, the surface topography changes can appear gradual and less abrupt than the implant 10 shown in FIG. 10.

Figure 12:
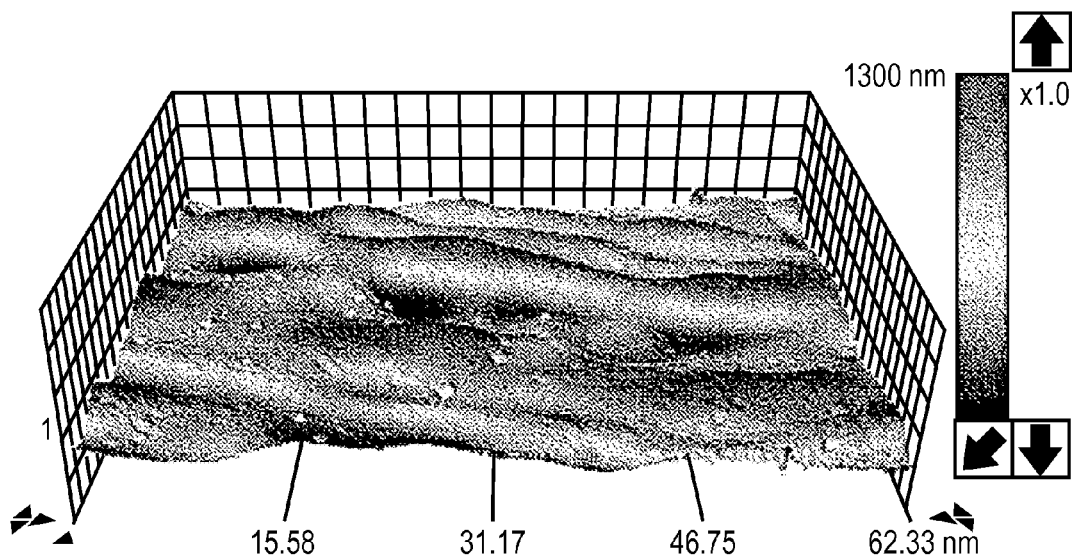
FIG. 12 shows an OP scan image of an implant surface after plasma treatment with Hexafluoropropylene (HFP).

FIG. 12 illustrates an example image of an OP scan of an implant 10 which has undergone a plasma treatment with HFP as a vapor deposition. The OP scan can illustrate gradual shaped features appearing on the surface of the implant at regular intervals. In addition, the patterns shown in FIG. 12 can appear different from the features shown along the implant in FIG. 11.

Figure 13:
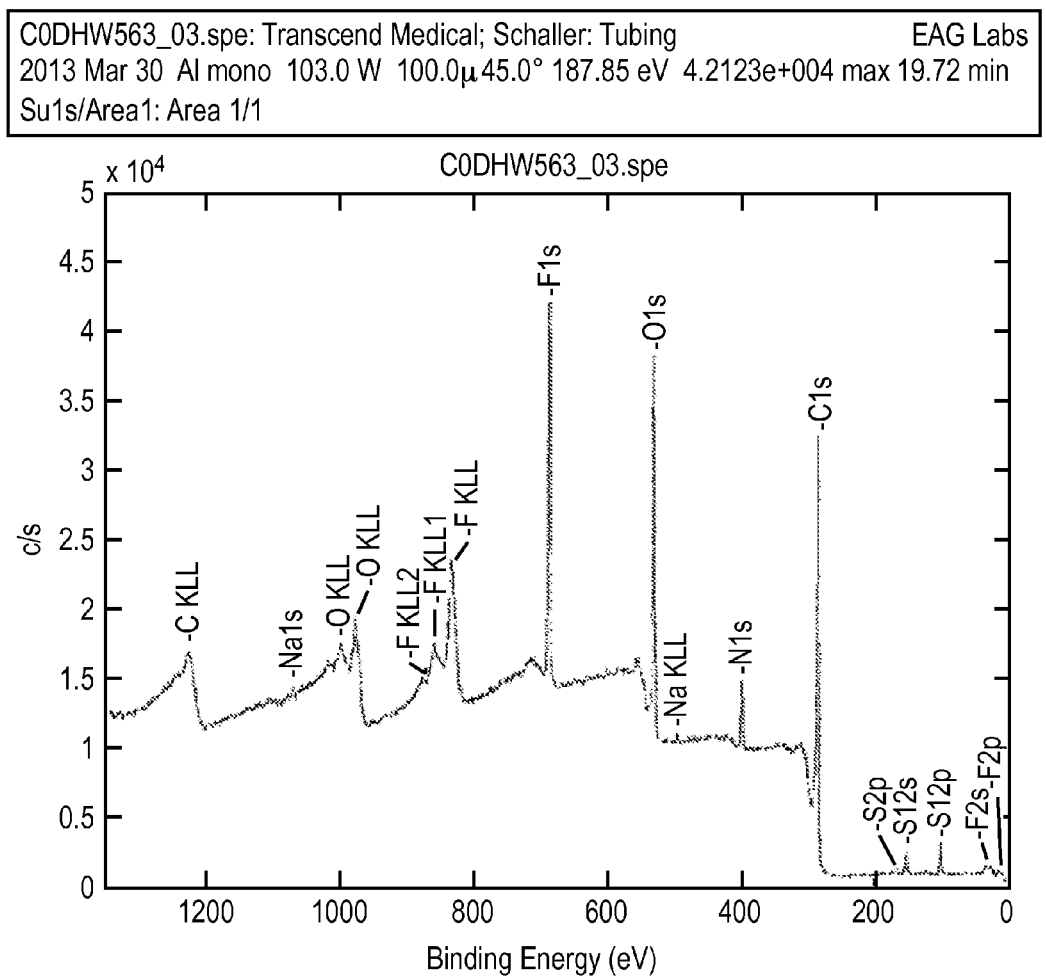
FIG. 13 shows results of X-ray photoelectron spectroscopy (XPS) of an implant surface after plasma treatment with HFP.

Additionally, FIG. 13 illustrates an example image of the implant 10 shown in FIG. 12 taken with an x-ray photoelectron spectroscopy (XPS). The XPS image can show the elemental composition of the surface of the implant 10. In addition, the surface chemistry can indicate a surface that is similar to a fluoropolymer, such as fluorinated ethylene propylene (FEP).

Table 1 illustrates example results of OP scans of implants 10 for each process listed in Table 1. As shown in Table 1, the average surface roughness (Sa) and the root-mean squared roughness (Sq) can vary significantly between the groups of implants 10 that were processed with different parameters. These results can demonstrate an embodiment for creating various surface topographies by varying the power, time, or material utilized in a plasma treatment.

Figure 14:
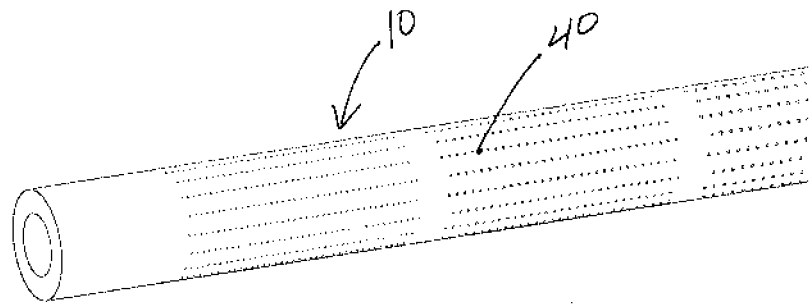
FIG. 14 shows an isometric view of an embodiment of the implant with divots.

FIG. 14 illustrates another embodiment of an implant 10 which includes a surface topography having lowered divots 40. The divots 40 can be arranged along any part of the implant 10 and in a variety of patterns and formations, including the linear formations shown in FIG. 14. The divots 40 can have a variety of shapes and dimensions. For example, one or more divots 40 can be circular and can be between approximately 0.1 microns to approximately 20 microns in diameter and approximately 0.1 microns to approximately 100 microns in depth. Alternatively or in addition, the divots 40 can be of any other shape including rectangular, ovular, and the like.

In some embodiments, any one of the divots 40 can be holes that go completely through the wall of the implant 10. In addition, in some embodiments, the divots 40 can be spaced at a distance of approximately 1 micron to approximately 1000 microns apart from one another, including at regular intervals. Alternatively the intervals may be irregular and the divots 40 may not form a specific pattern.

The divots 40 can be manufactured by any number of processes. For example, ablative processes such as laser ablation and chemical ablation may be used to remove areas of material, including the divots 40. In some embodiments, a laser ablative process may be accomplished with an excimer laser to create micro-sized divots 40 into the material of the implant 10, such as along the surface of the implant 10. Alternatively, other processes such as micromachining, molding, surface imprinting, and the like may be used to create an implant surface with divots 40. In addition, the divots 40 can be manufactured through additive processes that build layer upon layer and produce specific geometries along the surface of the implant 10.

Figures 20A, 20B:
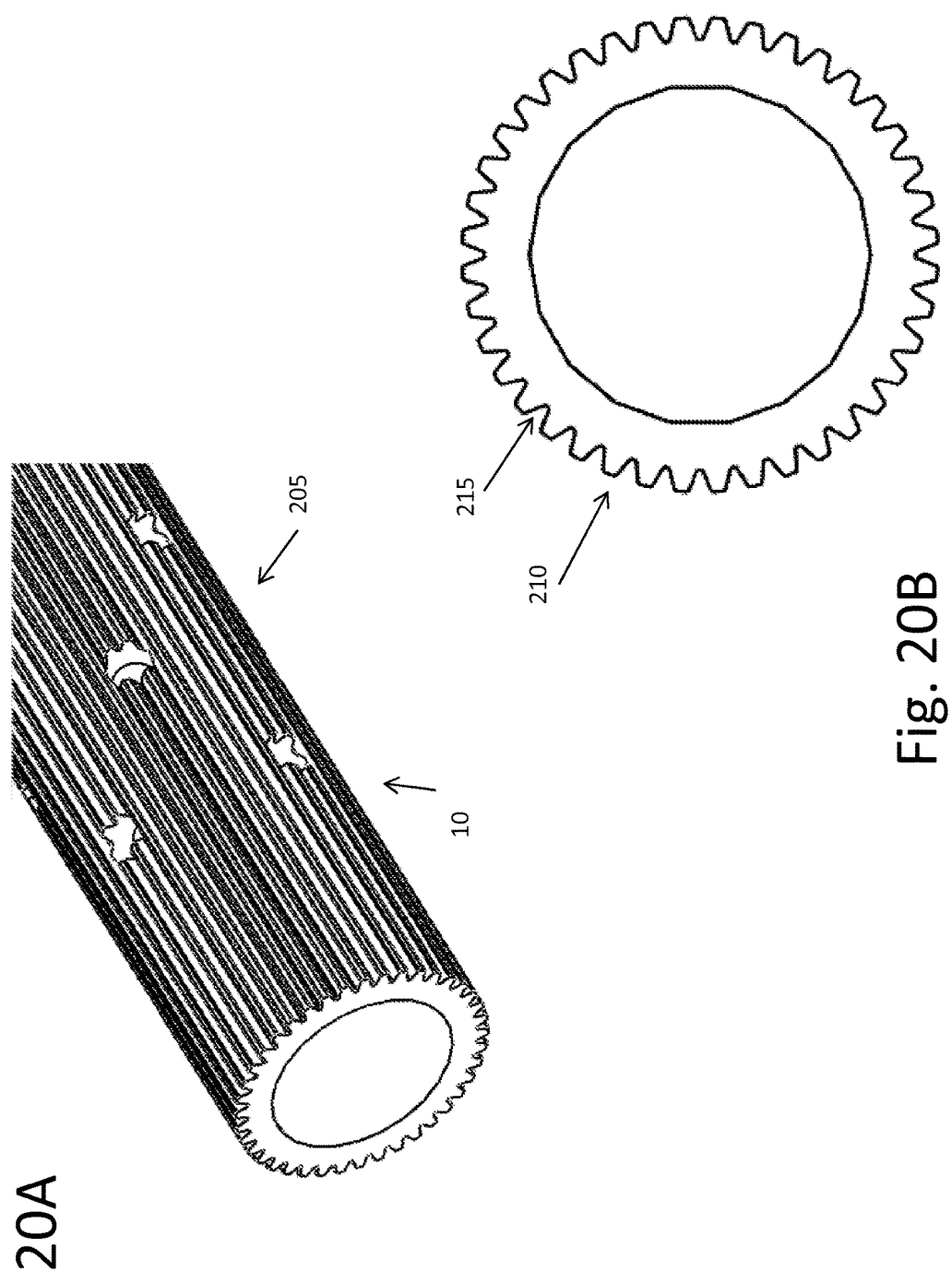
FIG. 20A shows an implant.
FIG. 20B shows a cross-sectional view of the implant of FIG. 20A.

FIG. 20A illustrates a perspective view of an embodiment of the implant with a series of micro-grooves 205. The micro-grooves 205 are aligned along the longitudinal axis of the implant. As shown in FIG. 20B. the micro-grooves 205 include a series of peaks 210 and valleys 215 which are arranged around the surface of the implant. Any number of dimensions may be used for the width of the peak 210 and valley 215, the height of the peak 210, depth of the valley 215, and number of features that occur around the surface of the implant.

The material of the implant 10 can be a plastic such as polyimide, PVDF, or any number of other implant grade plastics. Alternatively the implant 10 can be made out of a metallic material such as stainless steel, titanium, nitinol, or any number of other implant grade metals. In some embodiments, certain materials may be loaded into one or more divots 40. For example, drugs such as triamcinolone, dexamethasone, mitomycin, and the like may be deposited into the divots 40 like a reservoir and elute over time. Furthermore, the drugs may be mixed with an absorbable material such as poly-lactic acid (PLA) or poly-lactic co-glycolic acid (PLGA) or hyaluronic acid (HA), such as viscoelastic, or the like. These additional materials may allow the drug to elute slowly over time. Alternatively, there may be no drug but only the absorbable material which may elute over time to expose the divots 40 at some time after implantation but not immediately after implantation.

Figure 15:
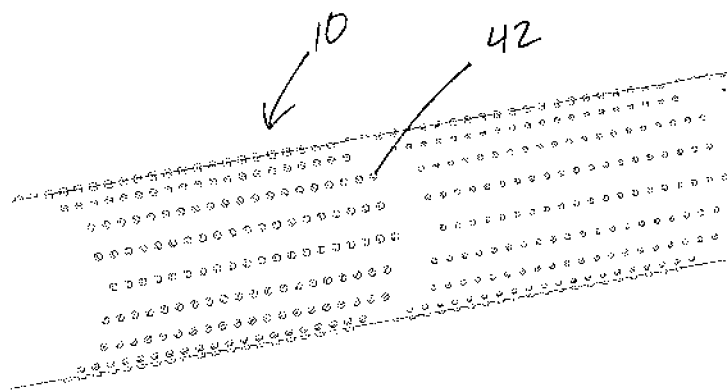
FIG. 15 shows an isometric view of an embodiment of the implant with bumps.

FIG. 15 illustrates an embodiment of the implant 10 having a surface topography including one or more bumps 42. The bumps 42 can be created in methods similar to those described above for the process of creating divots 40. In addition, the bumps 42 can be comprised of the same material as the implant 10 or can be composed of an alternate material that is deposited onto the surface of the implant 10, such as a plastic like PTFE or the like. Additionally, the bumps 42 can have any of a variety of shapes and sizes and be arranged in any number of patterns along one or more lengths of the implant 10.

Figure 16:
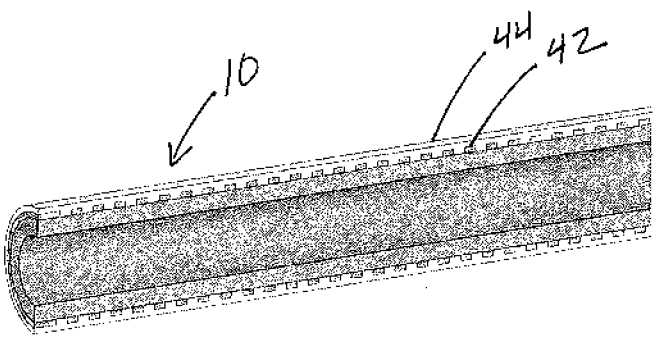
FIG. 16 shows an isometric view of an embodiment of the implant with bumps and a coating.

FIG. 16 illustrates an embodiment of the implant 10 having a series of bumps 42 and a coating 44 which can at least partially cover one or more of the bumps 42. The coating 44 can be comprised of any number of drugs or absorbable material or any combination thereof. In addition, the coating 44 can degrade over any period of time, such as approximately 1 hour to approximately 10 weeks. The coating 44 may be applied only to one or more discrete sections of the implant 10 while other sections may not be coated. Alternatively, multiple coatings 44 may be used at different locations to induce alternate physiological reactions.

In some embodiments, the implant 10 can be manufactured out of a polyimide tube using a dip coating process. The polyimide tube can then be laser ablated using an excimer laser in order to create micro divots along the implant, which can create a cratered surface. The size of the holes can be measured using optical measurement system under ×259 magnification and using SEM. The holes can range in diameter from approximately 35 microns to approximately 10 microns, and can be spaced evenly across the surface of the implant.

Figure 17:
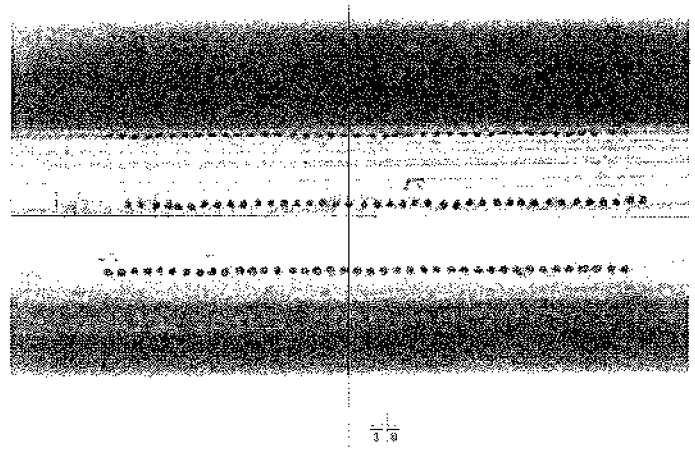
FIG. 17 shows a magnified image of an embodiment of the implant with divots.
Figure 18:
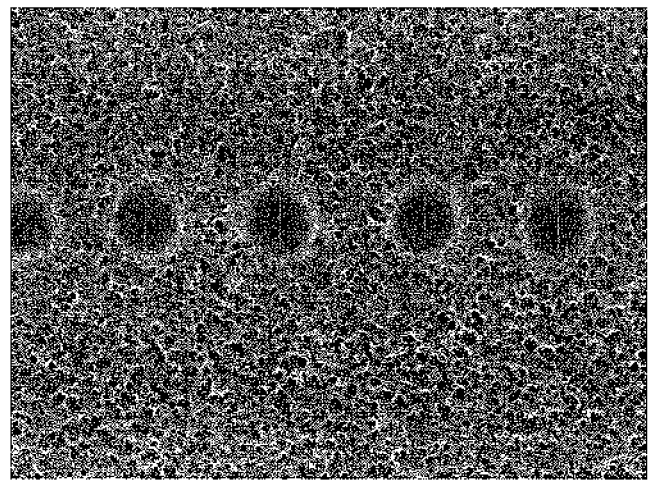
FIG. 18 shows an SEM image of an embodiment of divots arranged along a surface of an implant.

For example, FIG. 17 illustrates an image from an optical measurement which shows the size and shape of the divots 40 created in the range of approximately 10-15 microns in diameter. In FIG. 18, an example image is shown from an SEM analysis of the surface of the implant 10. The divots 40 shown in FIG. 18 are shown spaced approximately 20 microns to approximately 30 microns apart from one another but could be spaced at any distance. Additionally, any number of patterns could be created with the divots 40 and any number of distributions could be created with different divot 40 dimensions, including diameters.

As discussed above, any one or more of a variety of surface features or characteristics can be included with an implant 10, such as divots, peaks, bumps and coatings, in order to create a variety of tissue responses to the implanted implant. In addition, the variety of tissue responses can assist the implant 10 in reducing IOP by allowing the implant to create tenting and aqueous lake effects without interference from connective tissue growth.

Furthermore, the implant 10 can be positioned in any number of ocular tissues. For example, the implant 10 can be positioned into Schlemm's canal, under the conjunctiva, across the sclera, through the corneal sclera junction, behind the retina, above the cilliary body, within the capsular bag, underneath the iris, or in any number of alternate locations. Additionally, the surface of the implant 10 can be modified to promote or hinder the growth of any number of different tissue types. For example, the surface of the implant 10 can be configured specifically for interacting with connective tissue, reticular tissue, smooth cells, and the like.

In some embodiments, the implant can include a lumen which is partially or completely occluded with a bioabsorbable material. The bioasborbable material can be comprised of, for example, a polylactic acid (PLA), polylactic-co-glycolic acid (PLGA), any combination of these materials, or any other suitable degradable material. The bioabsorbable material can be configured to block the flow of fluid through the lumen during a post-operative period, such as, for example, the first week, first several weeks or first several months after implantation. The bioabsorbable material can assist in preventing tissue growth in the lumen of the implant during the post-operative period when foreign body reaction and inflammation may be highest. After a period of time, the bioabsorbable material may erode away and the lumen of the implant may become patent and allow fluid to flow through the lumen.

Additionally, either the proximal end or distal end of the implant can be radiused or chamfered in order to protect the eye from damage, such as from sharp edges. For example, at least one of the distal end and proximal end of the implant can be radiused or chamfered for promoting smooth insertion and interaction with surrounding tissue which can assist in minimizing cyclodialysis. Alternatively or in addition, either the proximal end or distal end of the implant can include features which assist in preserving or promoting fluid flow through the implant. Any number of a variety of proximal end or distal end shapes can be included in an implant implementation for assisting in preserving or promoting fluid flow through the implant.

Figure 19:
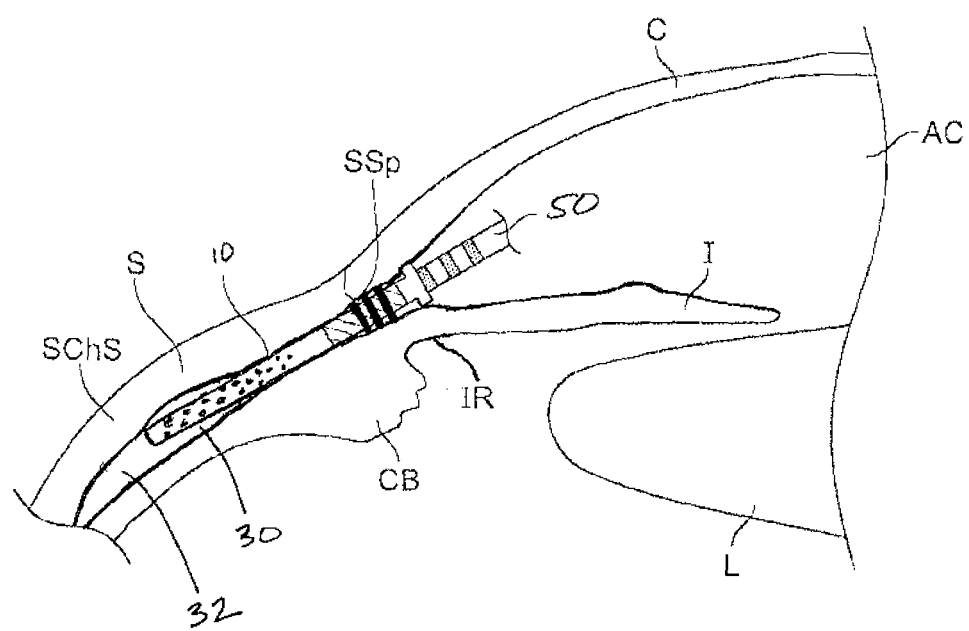
FIG. 19 shows an enlarged view of a section of an eye with an implant mounted on a guidewire approaching an implantation site from an anterior chamber of the eye.

FIG. 19 shows an enlarged view of the anterior region of the eye showing the anterior chamber AC, the cornea C, the iris I, and the sclera S. In addition, the implant 10 is shown as mounted on a guidewire 50 of a delivery device (not shown) and approaching an implantation site from the anterior chamber AC, such as by way of an ab-interno procedure. The implant 10 and guidewire 50 can move along a pathway such that the dissection entry point of the distal tip of the guidewire 50 can penetrate the iris root IR near its junction with the scleral spur SSp or the iris root portion of the ciliary body CB or other desired location.

The guidewire 50 with the implant 10 positioned thereupon can be advanced from a region of the anterior chamber, which can be viewed through a transparent zone of the cornea to a region of the anterior chamber that is obscured by the opaque zone of the cornea. The guidewire 50 and implant 10 can be advanced through the cornea until resistance is felt and a part of the delivery device can be seated at a location near the iris root, the ciliary body or the iris root portion of the ciliary body. The guidewire 50 can then be advanced further such that the guidewire 50 and implant 10 loaded thereon penetrate an area of fibrous attachment between the scleral spur and the ciliary body. This area of fibrous attachment can be approximately 1 mm. Once the distal tip of the guidewire 50 penetrates and is urged past this fibrous attachment region, the guidewire 50 can then more easily cause the sclera to peel away or otherwise separate from the ciliary body and possibly the choroid as it follows the inner curve of the sclera and enters the supraciliary or suprachoroidal space. A combination of the guidewire's tip shape, material, material properties, diameter, flexibility, compliance, coatings, pre-curvature etc. can make it more inclined to follow an implantation pathway that mirrors the curvature of the inner wall of the sclera and between tissue layers, such as between the sclera and the ciliary body and between the sclera and the choroid.

The dissection plane of the guidewire 50 and implant 10 can follow the curve of the inner scleral wall such that the implant 10 mounted on the guidewire 50 after penetrating the iris root or the iris root portion of the ciliary body can bluntly dissect the boundary between tissue layers of the scleral spur and the ciliary body such that at least the distal region of the implant 10 extends into the supraciliary space. In an embodiment, the implant 10 can be positioned such that it extends sufficiently past the scleral spur and is positioned between the tissue boundaries of the sclera and the choroid (the suprachoroidal space SChS). Once properly positioned, the implant 10 can then be released from the guidewire 50. The implant 10 can be permanently implanted into the eye or can be implanted for a shorter period of time.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

TABLE 1

| Plasma Gas, Power & Time | Sample Location | $S_a$ (nm) | $S_q$ (nm) | $S_p$ (µm) | $S_v$ (µm) | $S_z$ (µm) | $S_{sk}$ | $S_{ku}$ |
|---|---|---|---|---|---|---|---|---|
| Raw Polyimide | 1 | 24.93 | 31.17 | 0.14 | −0.27 | 0.41 | 0.10 | 3.83 |
| (Not cleaned) | 2 | 49.73 | 66.45 | 0.46 | −0.32 | 0.78 | 0.48 | 5.14 |
|  | 3 | 115.80 | 152.91 | 0.82 | −1.06 | 1.88 | 0.34 | 4.25 |
| $CF_4 + O_2$ | 1 | 49.46 | 78.92 | 1.28 | −1.89 | 3.18 | −0.48 | 21.71 |
| 200 $w$12 minutes | 2 | 58.48 | 79.98 | 1.34 | −1.32 | 2.66 | 0.36 | 8.65 |
|  | 3 | 143.84 | 187.93 | 1.40 | −1.43 | 2.83 | 0.60 | 4.81 |
| $H_2$ | 1 | 17.6 | 21.7 | 0.156 | −0.073 | 0.228 | 0.520 | 2.80 |
| 200 $w$12 minutes | 2 | 23.0 | 29.3 | 0.129 | −0.122 | 0.251 | 0.118 | 3.13 |
|  | 3 | 28.3 | 36.7 | 0.249 | −0.173 | 0.422 | −0.047 | 3.56 |
| $O_2$ | 1 | 16.1 | 20.0 | 0.113 | −0.090 | 0.203 | −0.139 | 2.80 |
| 200 $w$12 minutes | 2 | 51.5 | 65.2 | 0.274 | −0.286 | 0.560 | −0.092 | 3.43 |
|  | 3 | 31.0 | 40.9 | 0.130 | −0.149 | 0.279 | −0.677 | 3.48 |
| $CF_4 + O_2$ | 1 | 28.8 | 48.6 | 0.528 | −0.796 | 1.324 | −3.00 | 28.05 |
| 500 $w$12 minutes | 2 | 140.5 | 200.8 | 5.845 | −2.461 | 8.306 | −0.559 | 15.83 |
|  | 3 | 114.1 | 165.5 | 2.261 | −1.622 | 3.883 | −0.900 | 8.93 |
| Hexafluoropropylene | 1 | 11.86 | 15.52 | 218.51 | −207.16 | 425.66 | −0.40 | 12.42 |
| 500 $w$12 minutes | 2 | 92.96 | 116.19 | 367.03 | −457.76 | 824.79 | −0.07 | 2.90 |
|  | 3 | 20.45 | 26.41 | 212.32 | −304.64 | 516.96 | −0.18 | 5.90 |

What is claimed is:

1. A method of treating an ocular implant for creating surface features comprising:
    treating the ocular implant with a plasma treatment configured to alter a tissue response of the implant wherein the ocular implant includes an elongate tubular body comprising a proximal end, a distal end and a straight, inner lumen extending at least partway between the proximal end and the distal end, the implant having a fenestration extending from an outer surface of the tubular body and intersecting with the inner lumen, and wherein the implant includes an extruded feature extending from the outer surface of the tubular body adjacent the proximal end, and wherein treating the ocular implant includes treating a first length of the ocular implant with a first type of surface treatment and treating a second length of the ocular implant adjacent the distal end with a second type of surface treatment, and wherein the first type of surface treatment promotes tissue proliferation and the second type of surface treatment prevents tissue proliferation.

2. The method of claim 1, wherein the plasma treatment process creates a micro-layer of material on the surface of the implant which has a different surface chemistry from the substrate material of the implant.

3. The ocular implant of claim 2, wherein the micro-layer of material is a polyolefin resin.

4. The ocular implant of claim 2, wherein the micro-layer of material is a fluoropolymer.

5. The ocular implant of claim 2, wherein the micro-layer of material is a polyethylene glycol derivative.

6. The method of claim 2, wherein the plasma treatment is a plasma enhanced chemical vapor deposition process.

7. The method of claim 2, wherein the lumen is non-coiled.

8. The method of claim 1, further comprising implanting the ocular implant in an eye such that the distal end is in a suprachoroidal space or supraciliary space and the proximal end is in an anterior chamber of the eye.

* * * * *